United States Patent [19]

Islam et al.

[11] Patent Number: 4,543,966

[45] Date of Patent: Oct. 1, 1985

[54] BIOPSY NEEDLE

[75] Inventors: Abul B. M. A. Islam, Northolt; David R. Bevan, Carshalton Beeches, both of England

[73] Assignee: Downs Surgical PLC, Surrey, England

[21] Appl. No.: 610,883

[22] Filed: May 16, 1984

Related U.S. Application Data

[63] Continuation of Ser. No. 384,757, Jun. 3, 1982, abandoned.

[30] Foreign Application Priority Data

Jun. 10, 1981 [GB] United Kingdom ............... 8117836

[51] Int. Cl.$^4$ ............................................. A61B 10/00
[52] U.S. Cl. ................................................... 128/754
[58] Field of Search ............... 128/753, 754, 305, 310

[56] References Cited

U.S. PATENT DOCUMENTS

| | | | |
|---|---|---|---|
| 2,919,692 | 1/1960 | Ackerman | 128/754 |
| 3,007,471 | 11/1961 | McClure | 128/754 |
| 3,512,519 | 5/1970 | Hall | 128/754 |
| 3,628,524 | 12/1971 | Jamshidi | 128/754 |
| 4,163,446 | 8/1979 | Jamshidi | 128/754 |
| 4,177,797 | 12/1979 | Boylis et al. | 128/754 |
| 4,262,676 | 4/1981 | Jamshidi | 128/754 X |
| 4,356,828 | 11/1982 | Jamshidi | 128/754 |

FOREIGN PATENT DOCUMENTS

| | | |
|---|---|---|
| 542619 | 1/1942 | United Kingdom . |
| 1260173 | 1/1972 | United Kingdom . |
| 1323375 | 7/1973 | United Kingdom . |
| 1386215 | 3/1975 | United Kingdom . |
| 1437622 | 6/1976 | United Kingdom . |
| 1514019 | 4/1977 | United Kingdom . |
| 1500419 | 2/1978 | United Kingdom . |
| 646984 | 2/1979 | U.S.S.R. ............... 128/754 |

Primary Examiner—Edward M. Coven
Attorney, Agent, or Firm—Mason, Fenwick & Lawrence

[57] ABSTRACT

Biopsy needles comprising an elongate hollow needle having an inwardly tapered front end portion terminating in a cutting edge have been used for taking bone marrow biopsies, but difficulties occur, inter alia, in breaking off the biopsy from the remainder of the marrow and retaining it in the needle. This difficulty is overcome by the needle having a front end portion of smaller internal cross-section than the remainder of the needle, with an internal shoulder or step where the said front portion adjoins the wider internal portion of the needle. The shoulder is adapted to break or cut the biopsy from the remainder of the marrow and retain it within the needle.

16 Claims, 15 Drawing Figures

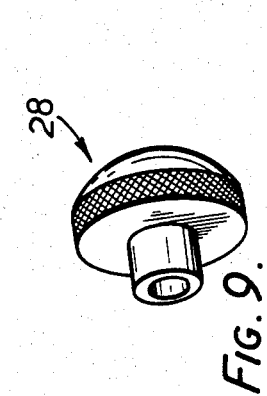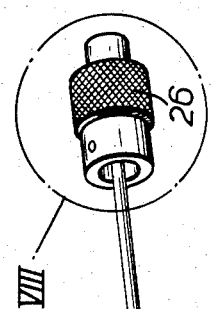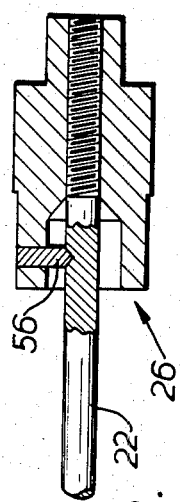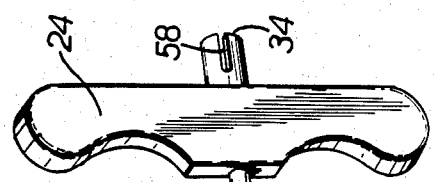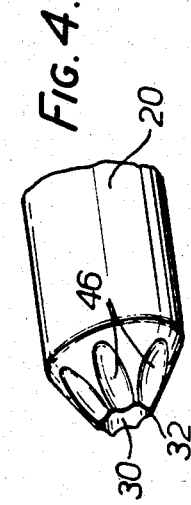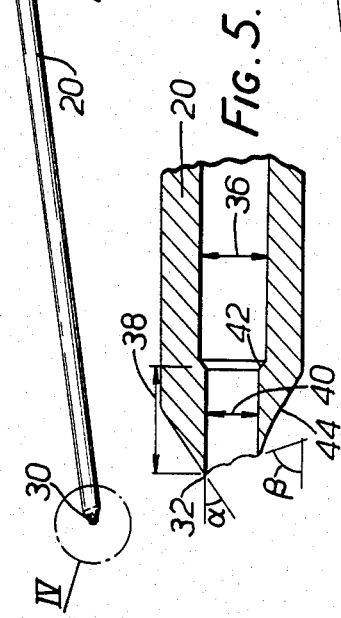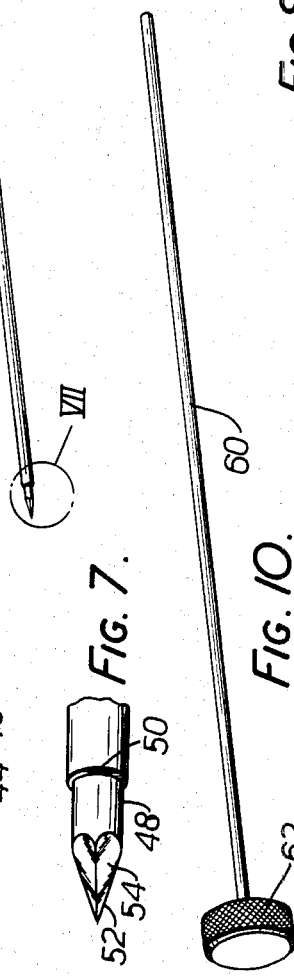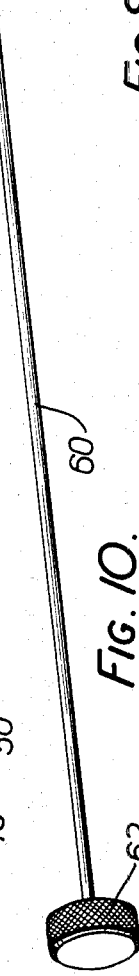

BIOPSY NEEDLE

This is a continuation of application Ser. No. 06/384,757, filed June 3, 1982, now abandoned.

The present invention relates to a biopsy needle and a biopsy needle assembly, particularly for use in taking bone marrow biopsies, and also to a method of taking a biopsy.

The value of bone marrow biopsy in the diagnosis of haematological as well as non-haematological malignancies is well established. Bone marrow biopsy is generally performed at the posterior iliac crest, in the lower spinal region. In carrying out such a biopsy, the biopsy needle has to be passed first through the skin and soft tissue and, secondly, through the bony cortex, before reaching the spongy bone containing bone marrow, and then it has to pass into, and sever the trabecular connections of, the spongy bone, and retain an adequate core sample thereof on withdrawal of the needle.

One biopsy needle assembly that is commonly used is that described in United Kingdom Patent Specification No. 1 252 170 (Jamshidi) (corresponding to U.S. Pat. No. 3,628,524). That biopsy needle assembly comprises an elongated hollow needle having open front and rear ends and a cutting edge at the front end, an elongated stylet having a closed front end and means to releasably position the stylet within the needle, the needle and stylet each having a uniform cross-section along a major portion of its length and an inwardly tapered front end portion, the arrangement being such that the needle and stylet are adapted to be inserted into tissue as a unit and, upon withdrawal of the stylet, the needle is adapted to be manipulated to cut a tissue sample which may be collected in the tapered end portion of the needle.

In using that needle assembly for bone marrow biopsy, an incision is made in the skin under local anaesthetic using a scalpel, and then the needle/stylet assembly is carefully advanced through the soft tissue and then through the bony cortex. The stylet here assists in penetrating the bony cortex: penetration of the bony cortex with the needle alone would be extremely difficult and would rapidly cause blunting of the needle. When the assembly enters the spongy bone containing marrow (indicated by decreased resistance to the advance of the assembly), the stylet is withdrawn and the hollow needle is slowly and carefully advanced, while being rotated in a clockwise-anticlockwise manner, so that an elongate core sample of the spongy bone containing marrow enters the hollow needle. When the needle has been advanced to the required extent, it is necessary to withdraw the needle to a small extent and then reinsert it such that the tip of the needle is directed at a slightly different angle, in order to sever the bony trabecular connections of the sample within the needle (that is to say, the biopsy) from the remainder of the spongy bone. Alternatively, the needle may, when in situ, be rocked or sulled slightly in order to sever the trabecular connections. The needle is then withdrawn from the patient, and the core sample is carefully pushed out through the rear end of the needle by means of a probe inserted through the front (cutting) end of the needle.

It has been found that, in practice, a number of difficulties occur with the use of that needle assembly. One important difficulty concerns the severing of the trabecular connections between the core sample within the needle and the remainder of the spongy bone. Experience has shown that, even when following one of the procedures described above, the trabecular connections are not always completely severed from the remaining spongy bone. In up to about 50% of cases, on withdrawing the needle it is found that the sample has fractured and that some of it has remained within the patient. Moreover, in up to about 5% of cases, the sample remains firmly attached at its base to to the remaining spongy bone and slips out of the needle during withdrawal of the needle and no sample is obtained at all. Thus, at best, the difficulty of carrying out the diagnostic tests on the sample is increased as the sample is of inadequate size and, in worse cases, it becomes necessary to perform another biopsy to obtain a further sample or even to obtain a sample at all.

A further important difficulty that arises is that the outer region of the elongate sample of spongy bone containing marrow is often found to be damaged and of no use for carrying out the necessary examination of the sample. That outer region tends to become crushed as the needle cuts through the spongy bone, both as a result of the cutting action of the needle and by the trabeculae being displaced within the spongy bone while advancing the needle. Thus, in general, only the axially central region, often only about the middle two-thirds measured radially, of the actual sample taken can be used for examination.

It will be appreciated that a combination of obtaining a sample of inadequate length and of only the central region of the sample being usable can cause severe difficulties in the interpretation of the sample.

A further disadvantage of the described needle assembly is that the hollow needle tends to become bent or otherwise damaged as a result of the rocking or sculling movement mentioned above.

The present invention provides a biopsy needle comprising an elongate hollow needle having a front internal portion and an adjoining second internal portion, wherein the said front portion is of smaller internal cross-section than the said second portion with an internal shoulder where the said front portion adjoins the said second portion.

The present invention also provides a biopsy needle comprising an elongate hollow needle having an open front end provided with a cutting edge and an open rear end, the hollow needle being of uniform internal circular cross-section throughout the major portion of its length and of narrower internal circular cross-section at its front end portion, there being an internal shoulder where the portion of narrower internal cross-section adjoins the major portion of wider internal cross-section, the needle being provided at its rear end with a handle means.

The present invention furthermore provides a biopsy needle assembly comprising a biopsy needle as defined immediately above, and an elongate trocar needle capable of being positioned within the elongate hollow needle and having a pointed front end, the assembly being capable of being inserted into and cutting through tissue and the hollow needle being such that on withdrawal of the trocar needle it can cut, receive and retain a tissue sample.

The portion of the hollow needle of narrower internal cross-section is preferably of uniform internal cross-section throughout its length, but it may alternatively taper internally toward the front end of the needle.

The dimensions of the trocar needle are preferably such that when fully inserted into the hollow needle through the rear end thereof the trocar needle fits snugly within at least the portion of the hollow needle of narrower internal cross-section, with its pointed end projecting beyond the front cutting edge of the hollow needle.

The trocar needle is preferably of uniform external circular cross-section throughout the major portion of its length and of narrower external circular cross-section at its front end portion, there being an external shoulder where the portion of narrower external circular cross-section adjoins the major portion of wider external cross-section, the dimensions of the trocar needle being such that when fully inserted into the hollow needle through the rear end thereof it fits snugly within the hollow needle with its pointed end projecting beyond the front cutting edge of the hollow needle.

The biopsy needle assembly preferably comprises first handle means attached to the rear end of the hollow needle, and second handle means attached to the rear end of the trocar needle.

One form of biopsy needle assembly according to the invention will now be described, by way of example only, with reference to the accompanying drawings, in which:

FIG. 3 is a perspective view of the hollow needle forming part of the biopsy needle assembly shown in FIG. 1;

FIG. 4 is an enlarged view of the portion IV indicated in FIG. 3;

FIG. 5 is a longitudinal cross-section through the portion IV shown in FIG. 4;

FIG. 6 is a perspective view of the trocar needle forming part of the biopsy needle assembly shown in FIG. 1;

FIG. 7 is an enlarged view of the portion VII indicated in FIG. 6;

FIG. 8 is a longitudinal cross-section through the portion VIII indicated in FIG. 6;

FIG. 9 is a perspective view of the domed handle means forming part of the biopsy needle assembly shown in FIG. 1;

FIG. 10 is a perspective view of a probe for use in conjunction with the biopsy needle assembly shown in FIG. 1;

Figure 1:
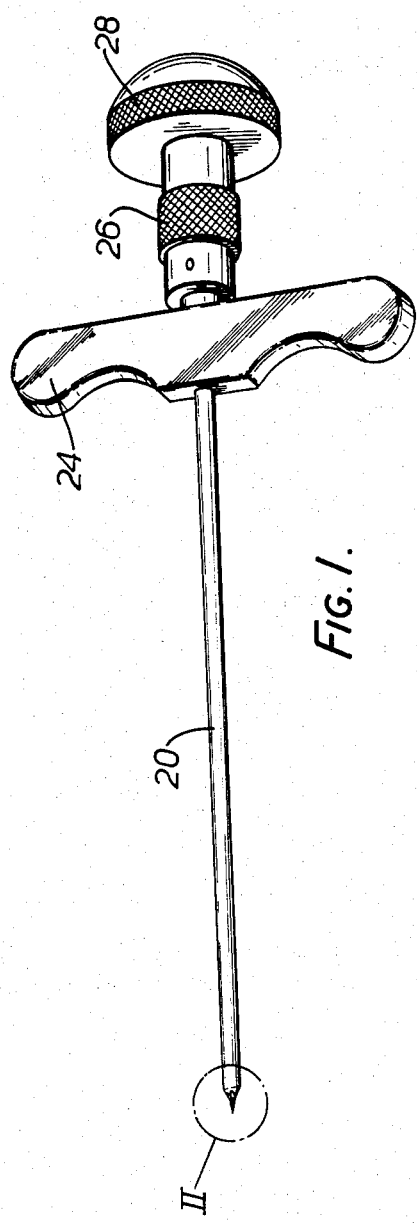
FIG. 1 is a perspective view of the biopsy needle assembly.
Figure 2:
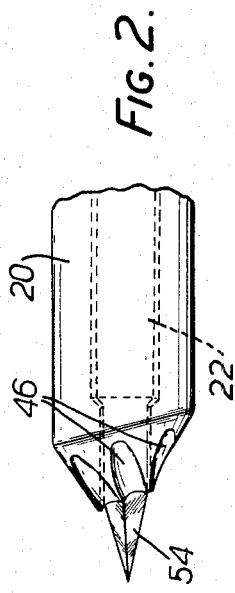
FIG. 2 is an enlarged view of the portion II indicated in FIG. 1.

The biopsy needle assembly (FIG. 1) comprises (i) an elongate hollow needle 20 (FIG. 3), (ii) a trocar needle 22 (FIG. 6), (iii) a first handle 24 (FIG. 3), (iv) a second handle 26 (FIGS. 6 & 8) and, optionally, (v) a third handle 28 (FIG. 9).

The elongate hollow needle 20 (FIGS. 3 to 5) has an open front end 30 provided with a cutting edge 32, and an open rear end 34. The external diameter of the hollow needle may suitably be from 2 to 4 mm, and its overall length may be from 110 to 150 mm. Throughout the major portion of its length, the hollow needle is of uniform internal circular cross-section 36 (FIG. 5), preferably with an internal diameter of from 1.5 to 3 mm, but the front end portion of the hollow needle is of slightly narrower uniform internal circular cross-section 40, with a small shoulder or step 42 where the narrower portion 40 adjoins the major, wider, portion 36. The maximum length 38 of the narrower portion 40 is preferably within the range of from 0.5 to 10 mm, especially from 2 to 5 mm. The difference between the internal diameter of the narrower portion 40 and that of the major, wider, portion 36 is preferably from 0.2 to 2 mm, especially from 0.2 to 0.5 mm; thus the width of the shoulder 42 is preferably from 0.1 to 1 mm, especially from 0.1 to 0.25 mm. The shoulder may be at right-angles to the internal walls of the hollow needle or may, for example, be at an angle of from 30° to 45° thereto (as shown in FIG. 5). With the exception of the tapered region adjacent to the cutting edge 32, the external diameter of the hollow needle 20 is substantially constant over the whole of its length and, in particular, the external diameter of the part of the hollow needle containing the shoulder 42 is the same or substantially the same as that of that part of the needle containing the portion of greater internal diameter 36. The hollow needle has a smooth external surface over at least the major portion of its length, in order to facilitate insertion of the hollow needle into the patient. The external surface of the hollow needle tapers, suitably at an angle α of from 30° to 60° to the longitudinal axis, at its front end 44 toward the cutting edge 32. The cutting edge 32 of the hollow needle lies in a plane that may be at an angle β of from 30° to 90°, preferably from 70° to 75°, to the longitudinal axis of the assembly. The use of an oblique angle β assists in achieving smooth cutting through the soft tissue, bony cortex and spongy bone. The cutting edge 32 is formed by means of a plurality (suitably from 4 to 10, preferably about 6 or 7) of shallow flutes 46 cut into the external surface of the hollow needle (FIG. 4), and extending suitably to the end of the tapered portion along the said surface. It has been found that the use of such flutes gives a particularly good and smooth cutting action.

The elongate trocar needle 22 (FIG. 6) is capable of being positioned within the hollow needle 20 to fit snugly therein when fully inserted into the hollow needle 20 through its rear end 34 (FIG. 1). Accordingly, it is of uniform external circular cross-section throughout the major portion of its length and is of slightly narrower external circular cross-section at its front end portion 48 (FIG. 7), with a small external shoulder 50 where the narrower portion 48 adjoins the major portion. The external diameter of the trocar needle 22 may suitably be about 1 mm less than the internal diameter of the corresponding portion of the hollow needle 20. The trocar needle has a pointed pyramidal front end 52, suitably with 3 or 4 facets 54, preferably 3 facets, each extending about 3 to 4 mm along the trocar needle, with sharp cutting edges where adjoining facets meet.

The first handle 24 (FIG. 3) is attached to the rear end of the hollow needle 20 and is in the form of a finger-grip extending from opposed sides of the rear end of the hollow needle 20 at right angles to its longitudinal axis.

The second handle 26 (FIG. 6) is attached to the rear end of the trocar needle 22, and is substantially cylindrical and coaxial with the trocar needle 22. The second handle 26 includes a peg 56 (FIG. 8) for co-operation with a slot 58 in the rear end 34 of the hollow needle 20 (FIG. 3) in order to prevent the trocar needle 22 from rotating within the hollow needle 20 when fully inserted therein (FIG. 1).

The third handle 28 (FIG. 9) is dome-shaped so as to be receivable in the palm of the operator's hand, and is adapted to co-operate with the first handle 24 when the trocar needle 22 is not inserted into the hollow needle 20, and to co-operate with the second handle 26 when the trocar needle 22 is so inserted (FIG. 1). In both cases, the arrangement is such that the operator can use and manipulate the needle by holding it with the dome-shaped third handle 28 in the palm of his hand and his fingers around the finger-grip first handle 24.

A probe or pusher rod 60 (FIG. 10), having a handle 62 at one end and a flat, blunt, other end, and having an external diameter such that it can be inserted through the front end of the hollow needle 20, may be used to push a tissue sample (biopsy) contained in the hollow needle 20 out through its rear end 34.

The biopsy needle assembly may be entirely of stainless steel but parts of the assembly that are not, in use, actually inserted into the patient may alternatively be of other materials. For example, the probe 60 and the handles 24, 26, 28 and 62 may be of chrome-plated brass, and the handles 28 and 62 may furthermore be of aluminium or of a plastics material.

With the needle assembly assembled in the manner shown in FIG. 1, and an incision having been cut in the patient's skin under local anaesthetic, the tip of the trocar needle may be inserted into the patient and the assembly may be gradually advanced through the soft tissue and then through the bony cortex, by rotating the assembly in a clockwise-anticlockwise manner and pushing on the dome-shaped third handle 28, while holding the handles in the manner described above. It has been found that the arrangement of the pointed pyramidal front end 52 of the trocar needle 22 and the fluted and angled cutting edge 32 of the hollow needle 20 described above enables the assembly to cut through the soft tissue and the bony cortex in a particularly easy and clean manner. Moreover, the arrangement of the several handles 24, 26, 28 described above enable a significant amount of manual pressure to be applied to the end of the needle assembly, both in rotating the needle in a clockwise-anticlockwise manner in order to cut the tissue and in actually advancing the needle through the tissue, thus again rendering it relatively easy to pass the needle assembly through the soft tissue and bony cortex. When the spongy bone has been reached (indicated by decreased resistance to the advance of the assembly), the trocar needle 22 is withdrawn from the hollow needle 20 and the domed third handle 28 is detached from the second handle 26 and attached to the rear end 34 of the hollow needle 20. The hollow needle 20 may then be slowly and gently advanced into the spongy bone with smooth clockwise-anticlockwise movement. Here, the fluted and angled cutting edge 32 cuts through the spongy bone in a particularly clean manner and a bone marrow sample passes into the interior of the hollow needle 20. When the hollow needle has been passed into the spongy bone to a depth sufficient to obtain an adequate core sample of marrow tissue—and here the procedure differs in an important respect from that necessary with the previously described needle—it is merely necessary to rotate the hollow needle about its longitudinal axis several times in order to sever the trabecular connections (instead of having to rock or scull it or withdraw it slightly and reinsert it at a different angle) and then slowly withdraw the needle.

Surprisingly, the small shoulder or step 42 not only functions to support the biopsy, in this case the sample of marrow, in the wider portion of the hollow needle and enables it to be retained within the hollow needle in a particularly effective and simple manner since the core expands somewhat in the wider portion 36, but is also provides the narrow front portion 40 which acts as a cutting blade along its length when the needle is rotated before withdrawal, to ensure complete severing of all trabecular connections which might hold the core back within the patient. Thus the risk of the biopsy sample remaining within the patient and of there being insufficient tissue extracted for interpretation purposes, or even of it being necessary to perform another biopsy, is substantially removed. Moreover, in contrast to the samples obtained using the previously described needles, the outer regions of the sample remain substantially undamaged.

Figure 11:
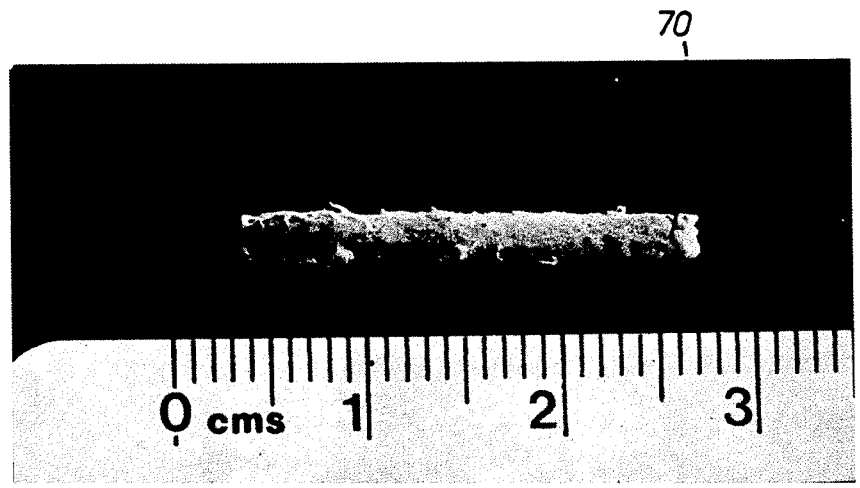
FIG. 11 is an enlarged photograph of a typical marrow core sample obtained using the biopsy needle shown in FIG. 3.

An enlarged photograph of a plan view of a typical marrow core sample 70 obtained using the biopsy needle shown in FIG. 3 is shown in FIG. 11. The actual size of that sample 70 may be seen from the scale, and a similar complete core sample is generally obtained on each attempt.

A photomicrograph (x8) of a prepared section of a similar core sample 71 (FIG. 12) shows that the marrow is intact and the bony architecture undistorted. The core was processed in methyl methacrylate and semithin sections cut from the processed core were stained with May-Grünwald-Giesma stain.

Figure 12:
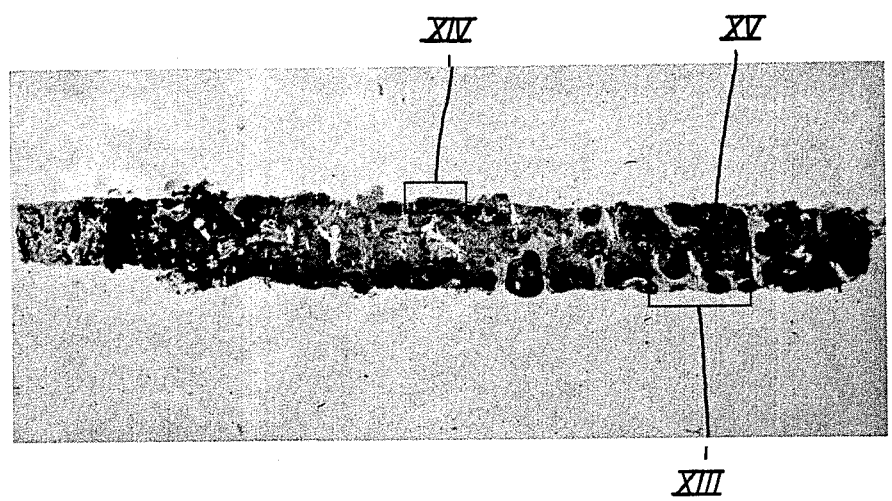
FIG. 12 is a low-power photomicrograph (x8) of a processed section through a marrow core sample similar to that shown in FIG. 11.
Figure 13:
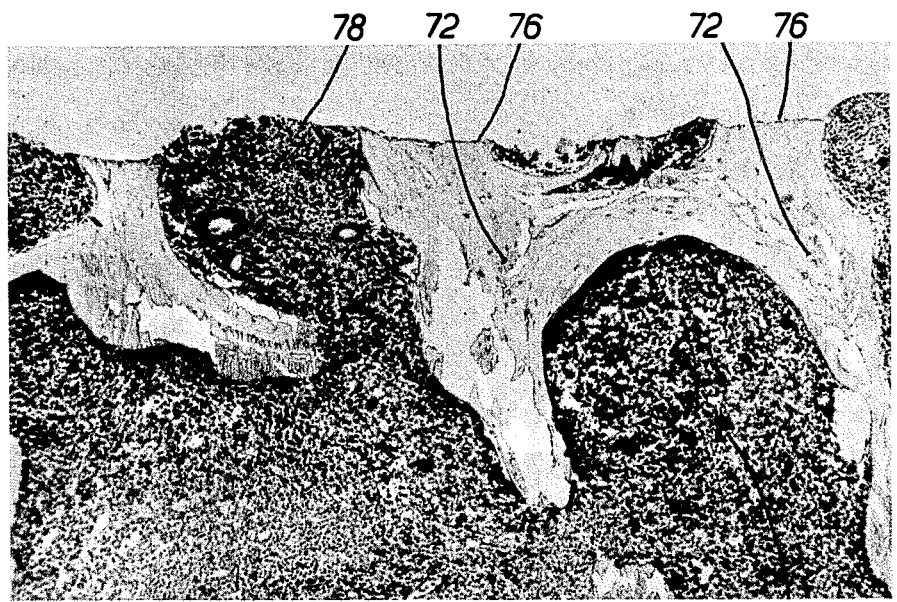
FIG. 13 is a higher power (x60) photomicrograph of the portion XIII of the section shown in FIG. 12.
Figure 14:
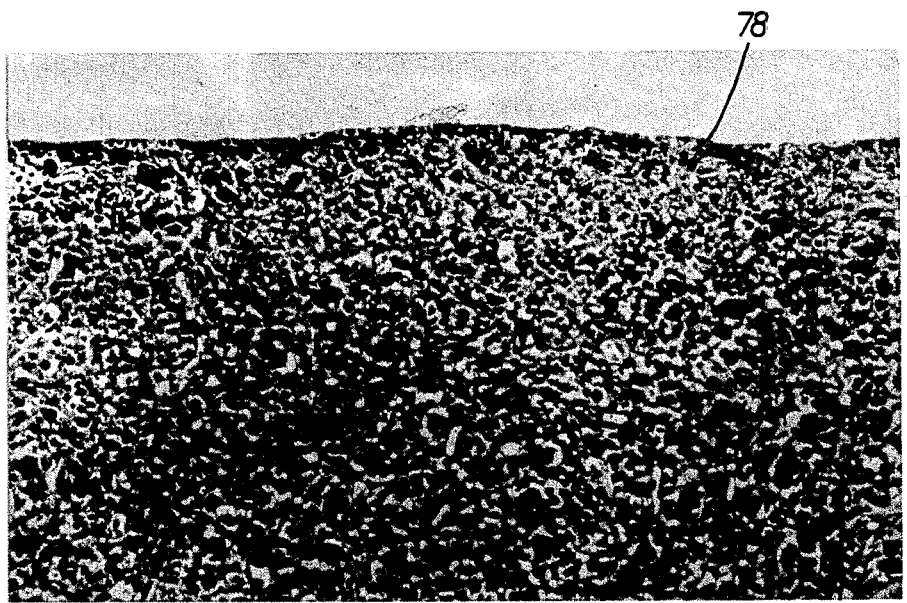
FIG. 14 is a higher power (x150) photomicrograph of the portion XIV of the section shown in FIG. 12.

A higher power (x60) photomicrograph (FIG. 13) of the portion XIII of the section shown in FIG. 12 clearly shows the trabeculae 72 and bone marrow 74 with clean-cut edges 76, 78 respectively, demonstrating the clean severing of both the trabeculae 72 and marrow 74. A still higher power (x150) photomicrograph (FIG. 14) of the portion XIV of the section shown in FIG. 12 clearly shows the marrow 74 having a clean-cut edge 78 with little crushing or artificial change.

Figure 15:
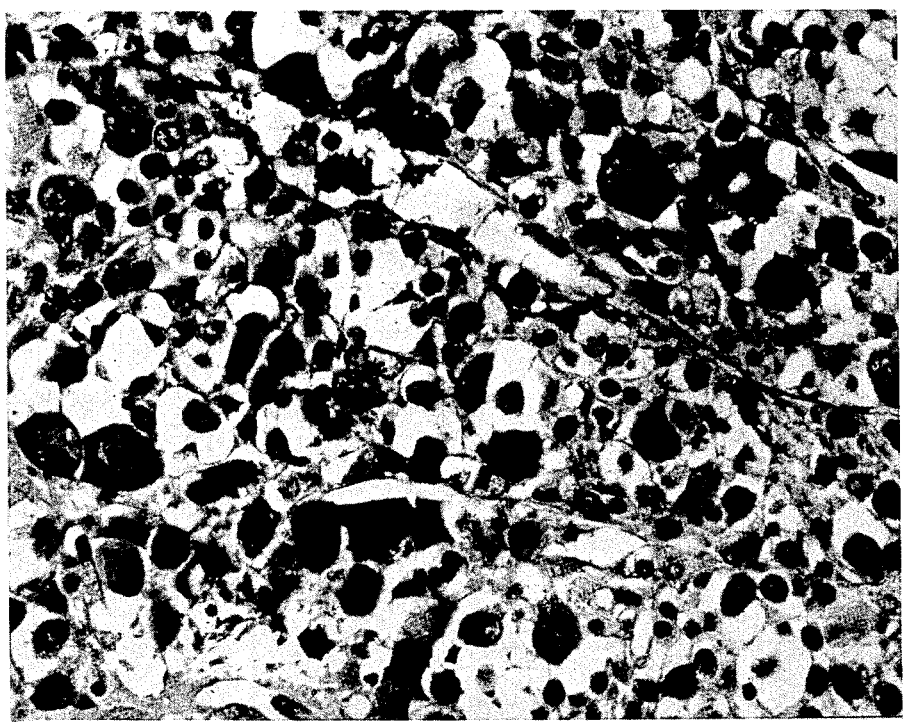
FIG. 15 is a high power (x600) photomicrograph of the portion XV of the section shown in FIG. 12.

A still higher power (x600) photomicrograph (FIG. 15) of the portion XV of the section shown in FIG. 12, shows absence of crushing and thus provides excellent cytomorphological detail.

Thus, not only do the needle and needle assembly according to the invention ensure that a sample of adequate length is extracted, but also that a substantially greater proportion of the sample actually extracted is available for interpretation.

We claim:

1. A biopsy needle for taking bone marrow biopsies comprising an elongate hollow needle having an open front end provided with a cutting edge and an open rear end, said hollow needle having throughout the major portion of its length a smooth uninterrupted cylindrical external surface of substantially constant diameter, and an elongated sample receiving chamber extending rearwardly from said open front end and defined by first and second cylindrical internal and integral sample-contacting surfaces, said first cylindrical internal surface being a portion of wider internal substantially constant diameter throughout a major portion of the length of said sample receiving chamber, and said second cylindrical internal surface being of narrower substantially constant internal diameter and defining the front end portion of said sample receiving chamber so that movement of a bone marrow biopsy into the narrower diameter front end portion and subsequent removal from the wider diameter portion is effected without any substantial crushing of the biopsy, said narrower diameter front end portion having an axial length in the range of 0.5 to 10 mm, there being an internal sample-retaining shoulder where said portion of narrower internal diameter adjoins said major portion of wider internal diameter, said cylindrical surfaces of wider and narrower diameters being coaxial and manipulating means provided at the rear end of said needle.

2. A biopsy needle as claimed in claim 1, wherein said cutting edge of said hollow needle lies in a plane that is at an angle to the longitudinal axis of the assembly that is within the range of from 30 degrees to 90 degrees.

3. A biopsy needle as claimed in claim 2, wherein said angle is within the range of from 70 degrees to 75 degrees.

4. A biopsy needle as claimed in claim 1, wherein said cutting edge of said hollow needle is formed by means of a plurality of shallow flutes in the external surface thereof.

5. A biopsy needle as claimed in claim 1, wherein the external surface of said hollow needle tapers at its front end toward said cutting edge.

6. A biopsy needle as claimed in claim 1, wherein the difference between the internal diameter of said portion of said hollow needle of narrower internal diameter and that of said major portion of wider internal diameter is within the range of from 0.2 to 2 mm.

7. A biopsy needle as claimed in claim 1, further comprising an elongate trocar needle capable of being positioned within said elongate hollow needle and having a pointed front end.

8. A biopsy needle as claimed in claim 7, wherein the dimensions of the trocar needle are such that when fully inserted into said hollow needle through the rear end thereof said trocar needle fits snugly within at least said portion of the hollow needle of narrower internal diameter, with its pointed end projecting beyond said front cutting edge of said hollow needle.

9. A biopsy needle as claimed in claim 7, wherein said trocar needle is of uniform external cylindrical shape throughout the major portion of its length and of narrower external cylindrical shape at its front end portion, there being an external shoulder where said portion of narrower external cylindrical shape adjoins said major portion of wider external cylindrical shape, the dimensions of said trocar needle being such that when fully inserted into said hollow needle through the rear end thereof it fits snugly within said hollow needle with its pointed end projecting beyond said front cutting edge of said hollow needle.

10. A biopsy needle as claimed in claim 7, wherein said pointed end of said trocar needle is pyramidal.

11. A biopsy needle as claimed in claim 7, further comprising trocar needle handle means attached to the rear end of said trocar needle.

12. A biopsy needle as claimed in claim 11, wherein said manipulating means comprises hollow needle handle means including means connecting it to said trocar needle handle means to prevent rotation of said trocar needle within said hollow needle when fully inserted therein.

13. A biopsy needle as claimed in claim 12, wherein said hollow needle handle means is in the form of a finger-grip extending from opposed sides of the rear end of said hollow needle at right angles to its longitudinal axis, said trocar needle handle means is substantially cylindrical and is coaxial with said trocar needle and additionally including a third, dome-shaped, handle means capable of being received in the palm of the user's hand, to cooperate with said hollow needle handle means when said trocar needle is not inserted into said hollow needle, and to cooperate with said trocar needle handle means when said trocar needle is so inserted.

14. A biopsy needle as claimed in claim 11, wherein said hollow needle handle means is in the form of a finger-grip extending from opposed sides of the rear end of said hollow needle at right angles to its longitudinal axis.

15. A biopsy needle as claimed in claim 11, wherein said trocar needle handle means is substantially cylindrical and is coaxial with said trocar needle.

16. A biopsy needle as claimed in claim 7, additionally comprising a blunt-ended pusher rod for insertion through said front end of said hollow needle in order to push a tissue sample contained therein out through its rear end.

* * * * *